United States Patent [19]

Ibsen et al.

[11] Patent Number: 5,151,453

[45] Date of Patent: Sep. 29, 1992

[54] LIGHT-CURABLE IONOMER DENTAL CEMENT

[75] Inventors: Robert L. Ibsen; Donald R. Pacropis, both of Santa Maria; William R. Glace, Orcutt, all of Calif.

[73] Assignee: Den-Mat Corporation, Santa Maria, Calif.

[21] Appl. No.: 561,194

[22] Filed: Aug. 1, 1990

Related U.S. Application Data

[63] Continuation of Ser. No. 333,904, Apr. 6, 1989, abandoned.

[51] Int. Cl.⁵ .............................. C08F 2/50; C09K 3/00
[52] U.S. Cl. ..................................... 522/14; 523/115; 523/116; 524/406; 524/443
[58] Field of Search ................. 522/14; 523/115, 116; 524/406, 443

[56] References Cited

U.S. PATENT DOCUMENTS

| | | | |
|---|---|---|---|
| 4,659,751 | 4/1987 | Bowen | 523/116 |
| 4,674,980 | 6/1987 | Ibsen et al. | 523/116 |
| 4,746,686 | 5/1988 | Waller | 523/116 |
| 5,084,491 | 1/1992 | Kerby | 523/115 |

FOREIGN PATENT DOCUMENTS

WO8801859A 3/1988 World Int. Prop. O. .......... 525/115

Primary Examiner—Paul R. Michl
Assistant Examiner—Andrew E. C. Merriam
Attorney, Agent, or Firm—Spensley Horn Jubas & Lubitz

[57] ABSTRACT

Two-part dental cement systems based on glass ionomers which are curable on exposure to light. The dental cement systems comprise a two-part blend of sodium N(p-tolyl)glycine-glycidyl methacrylate (Na NTG-GMA) and pyromellitic dianhydride-methyl methacrylate (PMDM) resins and glass ionomers.

10 Claims, No Drawings

LIGHT-CURABLE IONOMER DENTAL CEMENT

CROSS REFERENCES TO CO-PENDING APPLICATIONS

This is a continuation of U.S. Ser. No. 07/333,904, filed Apr. 6, 1989, now abandoned.

BACKGROUND OF THE INVENTION

1. Field of the Invention

The present invention relates to dental cements It is more particularly directed to light-curable dental cements based on glass ionomers.

2. Description of the Prior Art

Ionomer cements are a recent advance in the practice of dentistry. Some of the better of such compositions are described in U.S. Pat. No. 4,738,722 to Ibsen, Glace and Pacropis. These cements have excellent adhesion and give minimal pulpal trauma, but tend to cure rather slowly, a disadvantage in many dental procedures.

SUMMARY OF THE INVENTION

The cements of this invention have all the advantages of the cements described in the Ibsen patent, and in addition, provide enhanced physical strength and bonding, but most importantly, have the ability to cure instantly on exposure to light.

DETAILED DESCRIPTION OF THE PREFERRED EMBODIMENTS

The cements of the present invention are a two-part system, each part of which can be packaged separately for storage and sale. These parts are mixed together just before use, thus insuring a fresh and vigorous cement.

There are two embodiments of the cements from which a dentist can choose, the selection depending on the viscosity needed. The first is a power/liquid, whose viscosity can be varied according to the powder/liquid ratio used when the powder and liquid are mixed. The second is a paste/paste, whose viscosity will be fixed when the pastes are mixed.

All cements of the present invention have the same components, whose concentrations will of course vary according to the viscosities desired.

These components are:

1. A glass. Any of the types customarily used in cements of this type can be employed, but a preferred type is that from which fluoride ions are leached. A glass which is especially preferred is an alumina fluoride silica glass made by Specialty Glass Company of Oldsmar, Fla., and designated SP912-1 Glass.
2. Barium tungstate.
3. Zinc oxide or titanium dioxide.
4. A bonding agent. As with the glass, any of those ordinarily used in cements of this type can be used, but those preferred for use are:
   NTG-GMA—alone or n combination with the sodium or other alkali metal salt of NTG-GMA. This material is made by the Esschem Corporation and believed to have the structure.

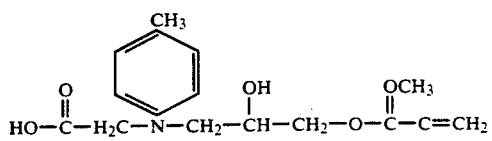

PMDM—also made by Esschem Corporation and believed to be a pyromellitic dianhydride extended with methyl methacrylate.
5. Ethyl 4-dimethylamino benzoate.
6. Ethoxylated bisphenol A dimethacrylate.
7. 2-hydroxyethyl methacrylate.
8. 2,3-bornanedione.
9. Butylated hydroxytoluene.
10. Polyacrylic acid, polymaleic acid, polyitaconic acid, or a copolymer of acrylic acid, maleic acid or itaconic acid. These polymers should have molecular weights $M_w$ of 3000–250,000, and can be easily prepared by conventional techniques. This component preferably contains about 5% of d-tartaric acids.
11. Benzoyl peroxide.

Components 2, 3, and 5–11 are commercially available.

The first embodiment of the present invention, the powder/liquid two part system, has the following composition:

Powder

Glass 65–90% by weight, preferably about 82%
Barium Tungstate 0–15%, preferably about 7%
Zinc oxide 0.0–10%, preferably about 2%
Equilibrium mixture of Na NTG-GMA with NTG-GMA 5–10%, preferably about 8%
Ethyl 4-dimethylamino benzoate 0.0–2%, preferably about 1%

Liquid

Ethoxylated bisphenol A dimethacrylate 50–80%, preferably about 73.71%
2-hydroxyethyl methacrylate 10–25%, preferably about 18%
PMDM 2.5–17%, preferably about 5%
Polyacrylic acid (or other polymer) 1–5%, preferably about 3.1%
2,3-bornanedione 0.05–0.25%, preferably about 0.14%
Butylated hydroxytoluene 0.01–0.08%, preferably about 0.03%
Benzoyl peroxide 0.005–0.05%, preferably about 0.02%
Tartaric Acid 0.10–1%, preferably about 0.12%

The powder and the liquid are made by mixing the listed components, in any order, under ambient conditions. To prepare the system for use, the powder and the liquid are mixed at a powder/liquid weight ratio of 2/1–1/1, as determined by the viscosity desired of the cement product.

The second embodiment of the present invention, the paste/paste two-part system, has the following composition:

Paste A

Glass 18–60%, preferably about 48%
2-hydroxyethyl methacrylate 5–15%, preferably about 7%
Ethoxylated bisphenol A dimethacrylate 20–50%, preferably about 27%
Equilibrium mixture of Na NTG-GMA with NTG-GMA 5–15%, preferably about 8%
Zinc oxide 0.0–15%, preferably about 2%
Barium Tungstate 0–15%, preferably about 7%
Ethyl 4-dimethylamino benzoate 0.0–2%, preferably about 1%

Paste B

Glass 25–65%, preferably about 57%

2-hydroxyethyl methacrylate 5-15%, preferably about 7%

Ethoxylated bisphenol A dimethacrylate 20-50%, preferably about 28%

2,3-bornanedione 0.05-0.30%, preferably about 0.1%

Butylated hydroxytoluene 0.005-0.10%, preferably 0.05%

Benzoyl peroxide 0.005-0.05%, preferably about 0.01%

Polyacrylic acid (or other polymer) 1-5%, preferably about 3%

PMDM 2.5-17%, preferably about 5%

The pastes are made by simply mixing the listed components, in any order, under ambient conditions. To prepare the system for use, the pastes are mixed in a paste A/paste B weight ratio of about 1/1.

MODE OF OPERATION

The dentist uses the system by combining the powder and liquid of embodiment 1, or the two pastes of embodiment 2, in the ratios desired, and then mixing them. The resulting cement is then applied to a tooth as needed, according to recognized principles of dental practice. The cement will self-cure in about 20-30 minutes, but cures instantly on exposure to light. Light having a wave length of about 480 nM at an intensity of about 5000 foot-candles is preferred. A exposure of about 30 seconds is sufficient to cure the cement in most applications.

Various modifications can be made to the present invention without departing from the apparent scope hereof.

We claim:

1. A two-part dental cement system composed of
a. a powder comprising:
   1. Alumina fluoride silicate glass
   2. Barium tungstate
   3. Zinc oxide
   4. Equilibrium mixture of Sodium N(p-tolyl)glycine-glycidyl methacrylate (Na NTG-GMA) with NTG-GMA
   5. Ethyl 4-dimethylamino benzoate; and,
b. a liquid comprising
   6. Ethoxylated bisphenol A dimethacrylate
   7. 2-hydroxyethyl methacrylate
   8. pyromellitic dianhydride-methyl methacrylate (PMDM)
   9. Polyacrylic acid
   10. 2,3-bornanedione
   11. Butylated hydroxytoluene
   12. Benzoyl peroxide
   13. Tartaric acid powder (a) and liquid (b) being stored separately and brought into use by mixing them in (a)/(b) weight ratios of 2/1-1/1.

2. The system of claim 1 in which the components are present in the following concentrations:
   1. 65-90%
   2. 0-15%
   3. 0.0-10%
   4. 5-10%
   5. 0.0-2%
   6. 50-80%
   7. 10-25%
   8. 2.5-17%
   9. 1-5%
   10. 0.05-0.25%
   11. 0.01-0.08%
   12. 0.005-0.05%
   13. 0.10-1%.

3. The system of claim 1 in which the components are present in the following concentrations:
   1. 82%
   2. 7%
   3. 2%
   4. 8%
   5. 1%
   6. 73.71%
   7. 18%
   8. 5%
   9. 3.1%
   10. 0.14%
   11. 0.03%
   12. 0.02%
   13. 0.12%.

4. A two-part dental cement system composed of:
a. a paste comprising:
   1. Alumina fluoride silica glass
   2. 2-hydroxyethyl methacrylate
   3. Ethoxylated bisphenol A dimethacrylate
   4. Equilibrium mixture of Na NTG-GMA with NTG-GMA
   5. Zinc oxide
   6. Barium tungstate
   7. Ethyl 4-dimethylamino benzoate; and,
b. a paste comprising:
   8. Alumina fluoride silica glass
   9. 2-hydroxyethyl methacrylate
   10. Ethoxylated bisphenol A dimethacrylate
   11. 2,3-bornanediol
   12. Butylated hydroxytoluene
   13. Benzoyl peroxide
   14. Polyacrylic acid
   15. pMDM paste (a) and paste (b) being stored separately and brought into use by mixing them in an (a)/(b) weight ratio of about 1/1.

5. The system of claim 4 in which the components are present at the following concentrations:
   1. 18-60%
   2. 5-15%
   3. 20-50%
   4. 5-15%
   5. 0.0-15%
   6. 0-15%
   7. 0.0-2%
   8. 25-65%
   9. 5-15%
   10. 20-50%
   11. 0.05-0.30%
   12. 0.005-0.10%
   13. 0.005-0.05%
   14. 1-5%
   15. 2.5-17%.

6. The system of claim 5 in which the components are present in the following concentrations:
   1. 48%
   2. 7%
   3. 27%
   4. 8%
   5. 2%
   6. 7%
   7. 1%
   8. 57%
   9. 7%
   10. 28%
   11. 0.1%

12. 0.05%
13. 0.01%
14. 3%
15. 5%.

7. A dental cement comprising the powder and liquid described in any of claims 1-3 mixed in a powder/liquid weight ratio of 2/1-1/1.

8. A dental cement comprising the pastes described in any one of claims 4-6 mixed in a paste (a)/paste (b) weight ratio of about 1/1.

9. A method for treating a tooth, the method comprising applying a cement according to any one of claims 7 and 8 to the tooth and then curing the cement.

10. The method of claim 9 wherein the curing is done by exposing the cement to light.

* * * * *